United States Patent [19]
Pfirrmann et al.

[11] Patent Number: 5,593,665
[45] Date of Patent: Jan. 14, 1997

[54] PHARMACEUTICAL COMPOSITIONS

[75] Inventors: Rolf W. Pfirrmann, Lucerne; Peter Geistlich, Stansstad, both of Switzerland

[73] Assignee: Ed Geistlich Söhne AG für Chemische Industrie, Wolhusen, Switzerland

[21] Appl. No.: 243,739

[22] Filed: May 17, 1994

Related U.S. Application Data

[63] Continuation of Ser. No. 46,933, Apr. 13, 1993, abandoned, which is a continuation of Ser. No. 778,988, filed as PCT/EP91/00524, Mar. 15, 1991, published as WO91/13628, Sep. 19, 1991, abandoned.

[30] Foreign Application Priority Data

Mar. 15, 1990 [GB] United Kingdom ................... 9005856

[51] Int. Cl.$^6$ .................................................. A61K 45/05
[52] U.S. Cl. .................................... 424/85.1; 514/422
[58] Field of Search ........................... 424/85.1; 514/422

[56] References Cited

U.S. PATENT DOCUMENTS

| | | | |
|---|---|---|---|
| 4,626,536 | 12/1986 | Pfirrmann | 514/222.5 |
| 4,980,160 | 12/1990 | Goldberg et al. | 424/85.1 |
| 5,210,083 | 5/1993 | Pfirrmann | 514/222.5 |

OTHER PUBLICATIONS

Bone, Roger C, Annals of Internal Medicine, vol. 115(6), pp. 457–469, 1991.
Glauser, M. P. et al., The Lancet, vol. 338, pp. 732–736, 1991.
Kilbourn, Robert G. et al., Jour. of the National Cancer Institute, vol. 84(11), pp. 827–831, 1992.
Natanson, Charles et al., Annals of Internal Medicine, vol. 120(9), pp. 771–783, 1994.
The Economist, "Panic in the Petri Dish", pp. 61–62, Jul. 23, '94.
Cross, Alan S et al., Infection and Immunity, vol. 61, No. 7, pp. 2741–2747, Jul. 1993.
Petros, Andy et al., The Lancet, vol. 338, pp. 1557–1558, 1991.
Tracey et al., Science, vol. 234, pp. 470–474, 1986.
Roitt et al. "Immunology", Publishes Niosby St. Louis, Third Edu., pp. 8.12–8.15, 1993.
Fink et al., J. Surgical Res., vol. 49, pp. 186–196, 1990.
McCartney et al., Bacterial Endotoxins, pp. 361–371, 1988.
Bedrosian, I. et al. "Taurolidine, an Analogue of the Amino Acid Taurine, Suppresses Interleukin and Tumor Necrosis Factor Synthesis in Human Peripheral Blood Mononuclear Cells", Cytokine, vol. 3, No. 6 (Nov.), 1991, pp. 568–575.
Glauser, M. P. et al, "Septic Shock: Pathogenesis", The Lancet, vol. 338, Sep. 21, 1991.
Monson, J. R. T. et al., British Journal of Surgery, vol. 77, No. 7, p. A708 (Jun. 1990).
Old, Lloyd J., "Tumor Necrosis Factor : Structure, Mechanism of Action, Role in Disease and Therapy", 2nd International Conference on Tumor Necrosis Factor and Related Cytokines, Napa. Calif., Jan. 15–20, 1989.
Chemical Abstracts, vol. 106, pp. 20–21, Abstract No. 43490j, (1987).
Chemical Abstracts, vol. 103, p. 34, Abstract No. 205594p, (1985).
Chemical Abstracts, 94, No. 23, abstract #185696p, 1981.

Primary Examiner—Chhaya D. Sayala
Attorney, Agent, or Firm—Rothwell, Figg, Ernst & Kurz

[57] ABSTRACT

The invention provides products containing tumour necrosis factor (TNF), and taurolidine and/or taurultam as a combined preparation for simultaneous, separate or sequential use for treatment of patients suffering from medical conditions mediated by TNF.

8 Claims, No Drawings

PHARMACEUTICAL COMPOSITIONS

This is a continuation of application Ser. No. 08/046,933, filed Apr. 13, 1993, which is a continuation of application Ser. No. 07/778,988, filed as PCT/EP91/00524, Mar. 15, 1991, published as WO91/13628, Sep. 19, 1991, both abandoned.

This invention relates to pharmaceutical compositions containing Tumour Necrosis Factor (TNF) and to compositions of use in medicine for combating the effects of Tumour Necrosis Factor.

Tumour Necrosis Factor was discovered by Carswell et al in 1975 (Proc. Nat. Acad. Sci. USA, 1975:72, c666–70) as a soluble factor released by the host after exposure to bacterial endotoxins and being responsible for tumour cytotoxicity. TNF has been shown to be a protein consisting of 157 amino acids. It has an apparent molecular weight of 17,350 by SDS-PAGE and of 45,000 gel filtration. Recombinant human TNF protein is now available in relatively large quantities. When the amino acid sequence of the molecule was determined, it was found that there are slightly differing forms of TNF and that TNF-alpha was identical to cachectin, a macrophage product believed to cause adverse host responses to bacterial invasion, including the wasting condition cachexia, and observed in the serum of tumour bearing animals.

TNF has been shown to have a wide range of biological activities in vitro. In addition to its antitumour effects, TNF is involved in immunoregulation, metabolism, haematopoiesis and musculoskeletal growth. Thus, TNF has been shown to lyse certain tumour cells, augment normal diploid fibroblast cell growth, induce differentiation of leukemic cells, inhibit certain haematopoietic progenitor cell growth, induce production of granulocyte-macrophage colony stimulating factor, modify structure and function of vascular endothelium, activate neutrophils and eosinophils, activate monocytes with resultant stimulation of IL-1 and prostaglandin E2 secretion, upregulate fibroblast expression of Class 1 MHC antigens, stimulate the production of prostaglandin E2 and collagenase in fibroblast and synovial cells, induce bone and cartilage resorption, inhibit proteoglycan synthesis, suppress lipoprotein lipase synthesis in adipocytes and prevent differentiation of preadipocytes to adipocytes. Recently, TNF has been reported as playing a role in the progression of AIDS related complex (ARC) to AIDS itself.

There is thus a wide range of medical conditions in which administration of TNF is indicated. However, TNF is very toxic. It appears to be responsible for many or all of the symptoms of endotoxaemia caused by lipopolysaccharide (LPS). Such toxicity clearly represents a serious problem in using TNF in therapy. Thus, in attempts to evaluate TNF in the treatment of cancer, clinical trials have shown that fever, chills, fatigue and headache were commonly observed. Inflammation was also observed at the injection site. Anaemia and hyperglycaemia have also been observed in test animals. Tests for the presence of antibodies to TNF have so far been uniformly negative.

We have found that the antibacterial compounds taurolidine and taurultam are significantly effective in reducing the toxicity and side effects of TNF. While we do not wish to be bound by theoretical considerations, it appears possible that taurolidine and taurultam interfere with synergism between TNF and endotoxins or metabolic products derived from endotoxins. This is supported by the finding that taurolidine and taurultam do not inhibit the antitumour effect of TNF but, in fact, augment such cytotoxicity. We have further found that taurolidine and taurultam do not have a significant cytotoxic effect against normal cells and may thus be safely used in combination with TNF in combating tumours.

Taurolidine and taurultam are closely related and have the formulae set out below:

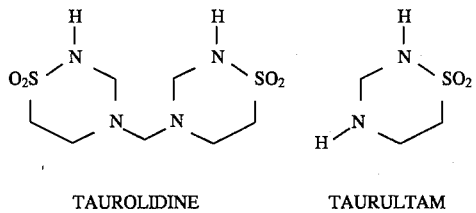

TAUROLIDINE                TAURULTAM

Both the above compounds are methylol tranfer agents. Taurolidine can tranfer three methylol groups to leave as a residue the very well tolerated compound taurinamide. Taurultam is, in fact, produced during the methylol transfer process of taurolidine, itself being capable of transferring a single methylol group to leave a residue of taurinamide. Thus, the two compounds are essentially equivalent.

As indicated above, the primary effect of taurolidine and taurultam is in reducing or eliminating the toxic side effects of TNF. Consequently, such combined therapy will also be beneficial in all of the other medical indications of TNF, in each of which the toxicity of TNF represents a negative indication. Taurolidine and/or taurultam do not need to be administered simultaneously with TNF or in the same composition although compositions containing both components are convenient.

According to one aspect of the invention we provide a method of treatment of medical conditions mediated by TNF wherein a patient suffering from one or more of such conditions is treated with effective amounts of TNF and of taurolidine and/or taurultam.

The invention also includes products containing tumour necrosis factor (TNF), and taurolidine and/or taurultam as a combined preparation for simultaneous, separate or sequential use for treatment of patients suffering from medical conditions mediated by TNF.

Thus the invention also provides a process of manufacturing a pharmacautical composition, wherein TNF is admixed with taurolidine and/or taurultam.

The invention further provides a use of taurolidine and/or taurultam to reduce the toxic side effects of TNF in the human or non-human animal body.

It is believed that other agents known to be involved in tumour metabolism may also advantageously be co-administered in conjunction with the above combined therapy. Such agents include gamma-interferon, interleukin-1 and interleukin-2. Cytotoxic agents such as adriamycin and actinomycin D may also be co-administered.

The active compounds here concerned will normally be administered by the parenteral route, for example intravenously. The compositions may thus comprise water for injection together with saline and other injectable components. The water-solubility of taurolidine is rather low and it may be advantageous to include one or more substances increasing the solubility of taurolidine and to a lesser extent taurultam, for example a polyol such as glucose. Such compositions are described in European Patent Application 253662.

TNF will be administered in accordance with the invention in the dose range 1 ng/kg to 100 ng/kg units such as ampoules for injection, will normally contain 1 ng to 100 ng, of TNF.

Taurolidine and/or taurultam will be administered at significantly higher doses, namely 150 mg/kg to 450 mg/kg per day, preferably 300 mg/kg to 450 mg/kg per day. Relatively large volumes of aqueous solutions containing taurolidine and/or taurultam will thus be administered containing, for example, 10 g to 30 g of taurolidine and/or taurultam. It may be convenient to administer these compounds by infusion in view of the relatively large volumes concerned, conveniently at intervals throughout the day.

As indicated above, TNF is believed to be the principle mediator of the adverse effects produced by bacterial sepsis. In view of the beneficial effect of taurolidine and taurultam in reducing the toxic effects of TNF, it is also beneficial to administer these compounds in any medical condition where TNF is active adversely. Taurolidine and/or taurultam can thus be advantageously administered in the treatment of sepsis. The half life of TNF in the vascular system is relatively short, for example 90–180 minutes. In sepsis, it appears to be liberated as a single major pulse. Consequently, taurolidine and/or taurultam are preferably administered prophylactically in conditions where septic shock and/or endotoxaemia are likely to occur.

However, there are certain conditions, notably obstructive jaundice, where TNF levels in the blood remain massively high. Similarly, where tumours produce TNF, resulting in many of the symptoms associated with endotoxaemia, administration of taurolidine and/or taurultam will be beneficial in alleviating such symptoms. The invention thus extends to the therapeutic administration of taurolidine and/or taurultam to patients suffering from tumours or other conditions in which TNF is chronically present in detectable amounts in the blood.

The following non-limiting Examples are provided to illustrate further the invention:

EXAMPLE 1—Solution

| | |
|---|---|
| Bis-(1,1-dioxo-perhydro-1,2,4-thiadiazin-4-yl)-methane (taurolidine) | 400 g |
| Polyvinylpyrrolidone (Kollidone 17) | 1000 g |
| Sterlile water to | 20 liters |

15 Liters double distilled pyrogen free water are filled into a 25 liter glass vessel with stirrer and intensive reflux device and heated to 50° C. with stirring. The taurolidine (400 g) is added followed by PVP (Kollidone 17; 1000 g). After dissolution, the solution is cooled and the pH adjusted to 6.0 with a few drops of 0.1N hydrochloric acid. The solution is then passed through an absorption filter to remove microorganisms and pyrogens and through a sterilising millipore filter before being filled into 100 ml vials which are finally autoclaved.

EXAMPLE 2—Solution

| | |
|---|---|
| Taurultam | 990 g |
| Sterile water ad | 22 liters |

The taurultam is dissolved in the sterile water and filled into sterile bottles, 250 ml in each.

EXAMPLE 3—Tablet

| | |
|---|---|
| Taurolidine | 550 g |
| Amylum maydis | 60 g |
| Kollidone 25 | 50 g |
| (polyvinylpyrrolidone) | |
| Plasdon XL | 20 g |
| Magnesium stearate | 6 g |
| Distilled water | 200 g |

1000 tablets, each containing 500 mg taurolidine, are produced by conventional means using the above formulation.

In an alternative tablet formulation, the amylum maydis is replaced by 60 g amylum orizae.

EXAMPLE 4—Solution

| | |
|---|---|
| Taurolidine | 440 g |
| Pharmaceutical gelatin | 88 g |
| Sodium chloride | 99 g |
| Sterile water to | 22 liters |

The components are dissolved in the sterile water, if necessary using gentle warming and sonication. The solution is then filled into sterile bottles, 500 ml in each.

We claim:

1. In combination: tumour necrosis factor (TNF) and a member selected from the group consisting of taurolidine, taurultam and a mixture thereof, for simultaneous, separate or sequential use for treatment of patients suffering from medical conditions mediated by TNF.

2. A combination as claimed in claim 1 comprising said TNF and said member selected from the group consisting of taurolidine, taurultam and a mixture thereof, in a preparation for sequential administration of said TNF and said member.

3. A method of treatment of medical conditions mediated by TNF comprising administering to a patient suffering from one or more said conditions effective amounts of TNF and a member selected from the group consisting of taurolidine, taurultam and a mixture thereof.

4. A method of treatment as claimed in claim 3, wherein said effective amounts of TNF and of said member selected from the group consisting of taurolidine, taurultam and a mixture thereof, are co-administered.

5. A pharmaceutical composition comprising TNF and a member selected from the group consisting of taurolidine, taurultam and a mixture thereof.

6. A process of manufacturing a pharmaceutical composition, wherein TNF is admixed with a member selected from the group consisting of taurolidine, taurultam and a mixture thereof.

7. A method of reducing toxic effects of TNF in a human or non-human animal body, comprising administering to a human or non-human animal body at least one member selected from the group consisting of taurolidine, taurultam, and a mixture thereof, so as to reduce toxic effects of TNF in said body.

8. A method of treatment of a patient suffering from TNF-producing tumor or obstructive jaundice, thereby resulting in a chronic, detectable amount of TNF in the patient's blood comprising administering an effective amount of a member selected from the group consisting of taurolidine, taurultam or a mixture thereof, to the patient.

* * * * *